United States Patent [19]

Winters et al.

[11] Patent Number: 4,500,525

[45] Date of Patent: Feb. 19, 1985

[54] PHARMACOLOGICALLY ACTIVE PYRAZOLO/4,3-C/PYRIDINES

[75] Inventors: Giorgio Winters, Milan; Alberto Sala, Monza; Domenico Barone, Milan, all of Italy

[73] Assignee: Gruppo Lepetit S.p.A., Italy

[21] Appl. No.: 466,701

[22] Filed: Feb. 15, 1983

[30] Foreign Application Priority Data

Feb. 17, 1982 [GB] United Kingdom ............... 8204722

[51] Int. Cl.$^3$ ................. A61K 31/435; C07D 471/04
[52] U.S. Cl. ..................................... 514/210; 514/227; 514/222; 514/254; 514/322; 544/58.6; 544/61; 544/127; 544/362; 546/119; 546/120
[58] Field of Search ............... 546/119, 120; 424/246, 424/248.53, 248.55, 250, 256, 263; 544/58.6, 61, 127, 362

[56] References Cited

PUBLICATIONS

Van Heyningen, J. Am. Chem. Soc., vol. 80, pp. 156–158, (1958).

Primary Examiner—Henry R. Jiles
Assistant Examiner—Bernard I. Dentz
Attorney, Agent, or Firm—William J. Stein; Stephen L. Nesbitt; Gary D. Street

[57] ABSTRACT

The present invention is directed to new pyrazolo/4,3-c/pyridines, the process for their preparation, the pharmaceutical compositions containing them and their use as pharmocologically active substances. The compounds of the invention possess cardiotonic, antihypertensive, CNS depressant, neuroleptic, and analgesic activity.

5 Claims, No Drawings

PHARMACOLOGICALLY ACTIVE PYRAZOLO/4,3-C/PYRIDINES

Pyrazolo pyridines of formula I:

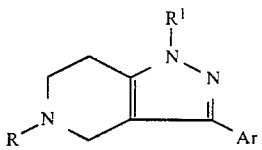

and their physiologically acceptable acid addition salts, wherein R represents hydrogen, $(C_1-C_{10})$alkyl, $(C_3-C_7)$cycloalkyl, $(C_1-C_6)$alkanoyl, halogen$(C_1-C_6)$alkyl, $(C_1-C_4)$alkoxycarbonyl, hydroxy$(C_1-C_6)$alkyl, phenyl, substituted phenyl, phenyl$(C_1-C_6)$alkyl, substituted phenyl$(C_1-C_6)$alkyl, phenyl$(C_1-C_6)$alkanoyl, substituted phenyl$(C_1-C_6)$alkanoyl, a group of the formula

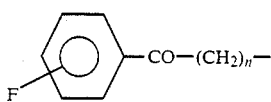

wherein n is an integer from 1 to 5 inclusive, or a group of formula:

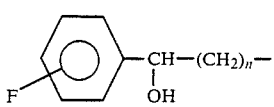

wherein n is as above;
or R is a group of formula

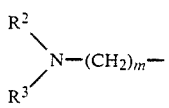

wherein m is an integer from 2 to 4 inclusive, $R^2$ and $R^3$ independently represent hydrogen, $(C_1-C_6)$alkyl, $(C_1-C_6)$hydroxyalkyl, $(C_1-C_4)$alkoxy, $(C_2-C_4)$alkenyl, $(C_2-C_4)$alkynyl, or $R^2$ and $R^3$ taken together with the adjacent nitrogen atom represent a (4-7) membered saturated heterocyclic ring which can optionally contain a further heteroatom selected from N, S, and O, and can bear a $(C_1-C_4)$alkyl group or a phenyl or substituted phenyl group, $R^1$ represents hydrogen, $(C_1-C_{10})$alkyl, $(C_3-C_7)$cycloalkyl, phenyl, substituted phenyl, phenyl$(C_1-C_6)$alkyl, substituted phenyl$(C_1-C_6)$alkyl, a group of formula:

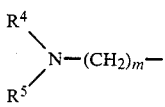

wherein m is an integer from 2 to 4 inclusive, $R^4$ and $R^5$ are as defined for $R^2$ and $R^3$ and Ar represents a phenyl or substituted phenyl group, or Ar is a 5-6 membered heteroaromatic ring, which can bear a $(C_1-C_4)$alkyl or phenyl substituents.

As used herein the term "substituted phenyl" alone or in combination refers to a phenyl group wherein one, two, or three hydrogens are replaced by groups each independently selected from chloro, bromo, fluoro, cyano, nitro, hydroxy, mercapto, trifluoromethyl, $(C_1-C_4)$alkyl, $(C_2-C_4)$alkenyl, $(C_2-C_4)$alkynyl, $(C_3-C_7)$cycloalkyl, $(C_1-C_4)$alkoxy, $(C_1-C_4)$alkylthio, $(C_1-C_4)$alkoxycarbonyl, carbo$(C_1-C_4)$alkyl, carbo$(C_3-C_7)$cycloalkyl, sulfinyl, $(C_1-C_4)$alkylsulfinyl, or a group of formula

wherein $R^6$ and $R^7$ are as defined above for $R^2$ and $R^3$. The term "4-7 membered saturated heterocyclic ring" encompasses for example also the following groups: azetidinyl, pyrrolidyl, piperidinyl, 4-aminopiperidinyl, 4-alkylamino-piperidinyl, piperazinyl, morpholinyl, thiomorpholinyl, 4-methylpiperazinyl, 4-phenylpiperazinyl, 2,6-dimethylpiperazinyl, 3,3-dimethylpiperazinyl, 2,6-dimethylmorpholinyl, and the like. "Halogen" as used in the present invention refers to chlorine, bromine, and fluorine atoms. "Acyl", whenever used in the description of the present invention includes $(C_1-C_6)$alkanoyl, benzoyl, and phenyl-$(C_2-C_6)$alkanoyl, wherein the phenyl group may be substituted as above. Examples of (5-6)membered heteroatom rings are: pyrrolyl, pyridyl, 4-aminopyridyl, 4-alkylaminopyridyl, thienyl, thiazolyl, oxazolyl, pyrazolyl and the like. "Physiologically acceptable salts" are pharmaceutically acceptable salts wherein the whole toxicity of the compound is not increased compared with the non-salt. From these, acid addition salts are obtained by treating compounds of formula I above with pharmaceutically acceptable acids.

As acids suitable for the formation of therapeutically acceptable salts there may be mentioned, for example, hydrohalide, sulfuric, phosphoric, and nitric acids; aliphatic, alicyclic, aromatic or heterocyclic carboxylic or sulfonic acids, such as formic, acetic, propionic, succinic, glycolic, lactic, malic, tartaric, citric, ascorbic, α-retoglutaric, glutamic, aspartic, maleic, hydroxymaleic, pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid.

These or other salts of the new compounds may also be used for purifying the resulting compounds by converting them into salts, isolating the latter and liberating the free bases from them. When according to the above outlined processes, compounds of formula I are obtained as the corresponding salts of pharmaceutically acceptable acids, they may be converted into the corresponding free base compounds with a suitable alkali agent. The free bases may in turn be transformed into the corresponding salts by reaction with predetermined pharmaceutically acceptable acids. In view of the close relationship between the new compounds in the free form and in the form of their salts what has been said above and hereinafter with reference to the free compounds concerns also the corresponding salts.

A preferred group of compounds of the invention are those compounds wherein R and $R^1$ are as above defined and Ar is a 4-substituted phenyl group.

An other preferred group of compounds of the invention are those in which R is hydrogen or $(C_1-C_6)$alkyl, $R^1$ is phenyl or phenyl$(C_1-C_6)$alkyl wherein the phenyl group may be substituted as above, and Ar is 4-halophenyl.

A further group of preferred compounds are those wherein R is hydrogen or $(C_1-C_6)$alkyl, $R^1$ is a 4-fluorophenyl group or a benzyl group wherein the phenyl group is optionally substituted as above, and Ar is a 4-fluorophenyl group.

The compounds of the present invention are useful as CNS depressant, neuroleptics, cardiotonic, antihypertensive, analgesic, and antiinflammatory agents. 7-Methylene pyrazolo/4,3-c/pyridines with antiinflammatory or CNS-depressant activity are described in German Pat. No. 2411499, U.S. Pat. Nos. 3,911,129, 4,065,617, 3,897,420 and 3,931,169, while U.S. Pat. No. 3,923,816 describes 7-thienyl, pyridyl, phenyl or alkyl-methylpyrazolo/4,3-c/pyridines.

A general outline of the present process for preparing the compounds of invention is described in the following scheme I:

SCHEME I

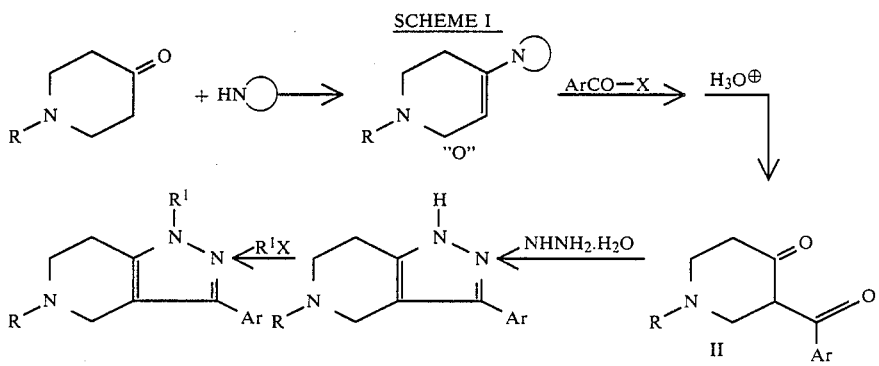

A suitable N-substituted-4-piperidone derivative, wherein the N-substituent is R as above defined, is reacted with a cyclic saturated secondary amine, in an inert organic solvent. Examples of cyclic saturated secondary amine are: morpholine, thiomorpholine, pyrrolidine, piperidine, and the like. The inert organic solvent, as used in the method of the present invention is a solvent in which the reactants are sufficiently soluble to allow the reaction to proceed, but which does not itself react with the functional groups of the reactants or of the final products. Inert organic solvents suitable in the above mentioned reaction step are, for example: benzene, toluene, xylene, and the like. The reaction preferably occurs in the presence of an organic acid which acts as a catalyst, such as for instance, p-toluenesulfonic acid. The reaction temperature may vary from room temperature to the reflux temperature, and preferably it is kept at about the reflux temperature. The compound of formula "O", that is recovered through common procedures, is reacted with the selected Ar-CO-X, wherein X is selected from chlorine and bromine, and Ar is defined as above, in the presence of an inert organic solvent. Examples of suitable inert organic solvents useful in this reaction step are: methylene chloride, chloroform, benzene, dioxane, and the like. The reaction is generally carried out in the presence of an acid binding agent such as tertiary amine, like TEA (triethylamine), TMA (trimethylamine), preferably in a molar amount or in a slight excess over the Ar-COX reactant. After stirring for a few hours, the mixture is acidified keeping the temperature between 0° C. and room temperature, and preferably below 15° C. The compound of formula II thus obtained is recovered through common procedures and reacted with a molar excess, preferably three or four times, of hydrazine hydrate. The reaction solvent is selected from lower alkanols, lower alkanoic acids, ethers or glycols and their ethers; one of the preferred solvents is ethyl alcohol. The reaction is generally carried out at room temperature. Following common practices, such as under vacuum distillation, extraction with solvents or precipitation from solvents, crystallization, chromatography, and the like, the compounds of formula I wherein Ar and R are defined as above and $R^1$ is hydrogen are obtained.

The compounds of formula I wherein Ar and R are as above, and $R^1$ is different from hydrogen can be obtained reacting the above compounds with the suitable $R^1X$, wherein X is chlorine, bromine or iodine, and $R^1$ is defined as above and different from hydrogen. This reaction is carried out by dissolving a compound of formula I wherein $R^1$ is hydrogen in an inert organic solvent such as, dimethylformamide, diethylether, tetrahydrofuran, dioxane, and the like, adding an alkali metal hydride (such as sodium or potassium hydride) suspended in mineral oil, or an alkali metal carbonate (such as potassium or sodium carbonate), at a temperature usually lower than 15° C. and then dripping into the obtained mixture a solution or a suspension of a molar amount or preferably a slight excess of the compound of formula $R^1X$ in the same solvent. The desired compound is finally recovered and purified through common procedures. The alkylation may occur at the 1 or 2 position. Generally, however, both isomers are obtained, but in quite different yields, and the 1-substituted isomer is always the major product. Probably the ratio between the two isomers depends on the different substituents at the pyrazolo pyridines ring and might be particularly related to the mesomeric and steric effects of the aryl substituent, even if also the reaction conditions can play a certain role in determining the final amount of the 1 or 2 isomer. The 2-substituted isomers of the compounds of formula I can be obtained from the mixture of isomers through common separation techniques and are encompassed within the scope of the present invention.

When the above described alkylation step is carried out starting from a compound of formula I in which Ar is as defined, R and $R^1$ both are hydrogen employing at least a twofold molar amount of alkylating agent, the derivative in which both R and $R^1$ are the same alkyl substituent is obtained. When lower amounts of alkylating agents are employed, a mixture of the two monoalkylated derivatives is obtained that can be separated by chromatography or another suitable separation technique. However, when the above starting compounds of formula I are treated with a RX derivative wherein R is a group of discrete steric hindrance, such as isopropyl, isobutyl, tert-butyl, neopentyl, and the like, only the 5-position is alkylated, while the 1-position still bears an hydrogen atom. The reaction is carried out in an inert organic solvent, in the presence of a strong alkali agent.

Examples of suitable solvents are: acetone, methylethylketone and other ($C_3$–$C_8$)ketones, dioxane and other ($C_4$–$C_8$)ethers, methylene chloride and other halogen($C_2$–$C_6$)alkyl solvents, and the like.

Suitable alkali agents are: alkali metal carbonates, hydrides, alkoxides, and the like.

A preferred embodiment is the further addition of a substance that acts as a catalyst, allowing a reduction of the reaction temperature and time. Examples of such catalysts are the alkali metal iodides.

The compounds of formula I wherein R and Ar are as above defined and $R^1$ is as defined but different from hydrogen, can also conveniently be prepared by directly reacting the suitable derivative of formula II with a hydrazine derivative of formula $R^1NHNH_2$. The reaction temperature is generally kept at about 0° C. during the addition, and then it is gently raised to room temperature or higher. The product is recovered through common procedures.

Following another embodiment of the invention, the compounds of formula I wherein Ar and $R^1$ are as above defined and R is an alkyl derivative are prepared by selectively reducing the corresponding acyl derivative, using one of a number of suitable reducing agents.

Even if the preferred reducing agent is lithium aluminium hydride in an inert organic solvent such as ethyl ether tetrahydrofurane, dioxane, benzene, toluene, and the like, other reducing agents that can usefully be employed in the reaction are: other aluminium hydride derivatives such as bis-isobutyl aluminium hydride; sodium, potassium or lithium borohydride (preferably in pyridine, in the presence of cobaltum chlorides), boron trifluoride etherate, diborane, and the like. When the alkyl derivative is a methyl derivative, it is preferably prepared by reacting the corresponding derivative of formula I, wherein R is hydrogen, with formic acid and aqueous formaldehyde preferably heated to a temperature of about 100° C. Concentrated aqueous formaldehyde is preferably about 40% aqueous formaldehyde.

The desired product is recovered following common working procedures, after alkalinization of the concentrated reaction mixture.

The compounds of formula I wherein Ar and $R^1$ are as above defined, and R is hydrogen can conveniently be prepared by hydrolyzing the corresponding acyl derivative, (such as the acetyl or the propanoyl derivatives). The hydrolytic step can be carried out employing one of the hydrolytic agents known in the art; however hydrohalic acids are found particularly useful. The product of the hydrolysis can be recovered as its acid addition salt, from which the free base can be obtained, or from the acid mixture before separating the salt, by means of a neutralization with a basic substance, such as a basic solution. Basic solutions which can usefully be employed are aqueous alkali metal hydroxide solutions, or the like.

Sometimes it is convenient to use stronger acidic conditions, such as those provided by hydrochloric or hydrobromic acid in glacial acetic acid. This is the case when it is desired to simultaneously hydrolyze other acid liable functions that may be borne by the Ar substituent. In fact, under the stronger acidic conditions outlined above, not only the N-acyl bond is hydrolyzed, but also the methoxy function at a phenyl group, and the like. Every reaction step of the procedures of the present invention can be monitored by means of TLC (thin layer chromatography).

The common procedures useful for the recovery of the products of the invention are, for example: extraction with solvents, in vacuo distillation, countercurrent extraction, precipitation by solvents, crystallization, chromatographic techniques such as column chromatography, preparative high performance liquid chromatography, and similar techniques known in the art.

The compounds of the invention were tested in vivo for their ability to compete with labelled ligands of $\alpha_1$, $\alpha_2$-adrenergic, and dopaminergic receptors. Said tests were made essentially following:

(a) the method described by B Jarrot et al., in Biochemical Pharmacology, Vol. 28, pp. 141–144, (1979), which uses the displacement of $^3$H-clonidine specifically bound in rat brain homogenate for the identification of substances interacting with the so called "$\alpha_2$-" adrenoceptor;

(b) the method described by P. Greengrass et al., European Journal of Pharmacology, Vol. 55, pp. 323–326, (1979), which uses the specific displacement of $^3$H-prazosin specifically bound in rat brain homogenate, for the identification of substances interacting with the so called "$\alpha_1$"adrenoceptor;

(c) the method described by P. M. Laduron et al., Biochemical Pharmacology, Vol. 27, pp. 323–328 (1978) and European Journal of Pharmacology, Vol. 49, pp 201–202 (1978), which uses the displacement of $^3$H-spiroperidol specifically bound in rat nucleous caudatus homogenate for identification of substances interacting with the brain dopaminergic receptor.

The above mentioned methods are radioligand binding assays and are based on the knowledge that many natural or synthetic physiologically active substances such as neurotransmitters, hormones, and others, specifically link to cellular receptors, generally of proteic nature. They are generally obtained from a tissue or organ of a suitable test-animal after isolation and homogenization of said tissue or organ.

The homogenate is twice centrifugated to separate and partially purify the receptorial fraction (synaptosomes).

The labelled substances employed are known to specifically bind their receptors, so the drug-receptor dissociation constants obtained for each test compound under standard conditions are a measure of their actual binding affinities. The validation of the above methods in predicting a possible pharmacological activity was carried out comparing the in vitro binding constants of a number of in vivo agonist or antagonist of the adrenergic or dopaminergic system with their in vivo activities. The $\alpha_1$-adrenergic activity is essentially correlated with a peripheral vasodilatation. The $\alpha_2$-adrenergic activity is essentially correlated with a hypotensive action of central origin, and the dopaminergic activity is correlated with a neuroleptic action. $IC_{50}$ values, defined as the drug concentration that cause 50% inhibition of the specific $^3$H ligant binding, are observed by incubating from 5 to 7 different dilutions of the tested compound in duplicate or triplicate. $K_i$, inhibition constant, values are calculated from the following formula:

$$K_i = \frac{IC_{50}}{1 + \frac{C}{K_D}}$$

wherein $IC_{50}$ is defined as above, C is the concentration of the $^3H$ ligand, and $K_D$ is the dissociation constant of the $^3H$ ligand-receptor complex.

The compounds of the invention display a $K_i$ value from about 0.3 to 3,000 nM on $^3H$ Prazosin binding, from about 900 to 3,000 nM on $^3H$ Clonidin binding, and from about 30 to 3,000 nM on $^3H$ Spiroperidol binding.

The results obtained with some representative compounds are summarized in the following Table:

| Compound of example No. | $K_1$ (nM) $^3H$ Prazosin |
| --- | --- |
| 19 | 69.2 |
| 32 | 92.2 |
| 95 | 32.2 |
| 96 | 52.0 |
| 100 | 14.7 |
| 103 | 11.1 |
| 105 | 6.23 |
| 106 | 0.331 |
| 107 | 23.6 |
| 108 | 7.48 |
| 110 | 40.3 |
| 111 | 12.9 |
| 112 | 24.2 |
| 113 | 17.3 |
| 114 | 17.3 |
| 116 | 7.24 |
| 117 | 38.6 |
| 118 | 14.5 |
| 119 | 5.86 |
| 122 | 8.70 |
| 123 | 13.0 |
| 128 | 21.2 |
| 132 | 20.8 |
| 133 | 12.4 |
| 134 | 6.35 |
| 135 | 47.2 |
| 136 | 21.9 |
| 138 | 40.3 |
| 139 | 20.6 |
| 140 | 73.5 |
| 141 | 32.8 |
| 142 | 36.3 |
| 144 | 8.14 |
| 145 | 49.4 |
| 146 | 30.9 |
| 147 | 20.1 |
| 150 | 18.3 |
| 151 | 15.2 |
| 162 | 97.6 |
| 163 | 42.4 |

The cardiovascular activity of the compounds of the invention was demonstrated in the spontaneously hypertensive rat as described by K. Aoki in Japan Cir. Journal, Vol. 27, p. 282, (1963). The arterial pressure was evaluated according to H. Fribel, E. Vredom, described in Arch. Exp. Phat. Pharmak. Vol. 232, p. 416, (1958). Some of the compounds of the invention show a lowering of the arterial pressure of at least 15% when administered at a dose inferior to 10% of the $LD_{50}$. This 15% threshold is generally considered predictive of significant antihypertensive activity. In particular, the compound of example 100 displayed a 30% lowering of the pressure in the above test when administered p.o. 50 mg/kg.

In renal hypertensive dogs, prepared essentially according to H. Golblatt, J. Linch. and R. F. Manzal, J. Exp. Med. 59, 347 (1934), some of the compounds of the invention show a considerable lowering of the systolic blood pressure without affecting the heart rate to a great extent.

The test compounds are administered orally and the pressure is measured according to the method of H. Friebel, E. Vrenden, Arch. Exp. Phat. Pharmak. 232, 419 (1558).

In the above test system the compound of example 100 determines a 20% drop of the blood pressure when administered 0.5 mg/kg p.o., the compound of example 106 determines a 22% drop when administered 1 mg/kg p.o., the compounds of Examples 134 and 135 determine a drop of 34% and 25%, respectively, when administered 5 mg/kg p.o., and the compound of example 107 determines a 43% drop of the blood pressure when administered 10 mg/kg p.o.

In addition, the compound of example 102 displays a good positive inotropic activity in conventional in vitro tests (such as those described in Pharmacological Experiments on Isolated Preparation, Livingstone, UK, 1970 and Eur. Journ. Pharm. 35, 235, and references therein). This activity is not due to $\beta$-adrenergic effects since it was not antagonized by propanolol.

The neuroleptic activity of the compounds of the invention was investigated by means of the "pole climbing avoidance test", as described by L. Cook et al. (Ann. N.Y. Acad. Sci. 66, 740, 1957) and subsequently modified by Maffii et al. (J. Pharm. Pharmac., 11, 129, 1959). As a representative example, the compound of example 38 scores as follows in the above test:

| Dosage (mg/kg, i.p.) | $CR_2$ | CR | UR |
| --- | --- | --- | --- |
| | (treated/untreated mice) | | |
| 10 | 9/10 | 3/10 | 0/10 |
| 25 | 10/10 | 8/10 | 0/10 |

The symbols CR, $CR_2$, and UR corresponds to the primary, secondary conditioned response and to the unconditioned response according to the above test.

The neuroleptic activity was investigated also by means of the "running fit". The test, which is well-know in the art, is based on the fact that a single injection of a high dose of morphine in mice induces a characteristic compulsive behaviour (the so called "running fit"). Neuroleptic drugs antagonize these effects of morphine and the treated animals recover an apparently normal behavior. The "runs" are counted and recorded through a dedicated automatic system.

The animals are divided into two groups, the treated (which receive the drug in the proper vehicle) and the control (which do not receive the drug but only the vehicle).

The schedule of treatments is as follows:
Administration of the drug (i.p. or p.o.) or the vehicle; after 30 minutes from this administration (60 minutes in the case of oral administration), the animals are treated s.c. with morphine (60 mg/kg). Following a 30 minutes resting time, the behavior of the animals is recorded for 15 minutes.

The results are calculated as percentage of inhibition of the running fit (treated/control × 100).

As a representative example, the compound of example 38 displays the following results in the above test:

| Dose (mg/kg) | % inhibition of the running fit |
|---|---|
| 7.5 (i.p.) | −42 |
| 10 (i.p.) | −60 |
| 20 (i.p.) | −89 |
| 25 (i.p.) | −96 |
| 25 (per os) | −79 |

The compounds of the invention may be administered by different routes. While the preferred routes of administration are oral and rectal, parenteral administration can also be employed.

For oral administration, the compounds are compounded into pharmaceutical dosage forms, such as, for instance, tablets, capsules, elixirs, solutions and the like. The dosage units may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives.

The dosage range is from about 0.01 to about 2.0 g per day, preferably administered in divided doses.

Accordingly, the present invention provides a therapeutic composition comprising as the active ingredient a compound of the invention together with a pharmaceutically acceptable carrier.

The following examples illustrate the manner in which the method of the invention can be practiced, but, as such, should not be construed as limiting the overall scope of the invention.

EXAMPLE 1:
5-Acetyl-3-(4-fluorophenyl)-4,5,6,7-tetrahydro-1H-pyrazolo/4,3-c/pyridine N-Acetyl-4-piperidone (1 mole) and morpholine (1.1 mole) in benzene (423 ml) are treated with 50 mg of p. toluensulfonic acid and refluxed for 8 hours in a Marcusson apparatus. The solvent is removed under reduced pressure and the residue is taken up with anhydrous methylene chloride (1000 ml). Triethylamine (1.1 mole) is added and the p-fluorobenzoylchloride (1.1 mole) dissolved in 200 ml of methylene chloride is dropped into the reaction flask at about 0° C. and +5° C. The reaction mixture is left at room temperature under stirring for 20 hours. Subsequently, 5% hydrochloric acid (1.270 ml) is added at 10° C. and stirring is continued for 30 minutes. The organic layer is separated, washed twice with water, dried over sodium sulphate, and evaporated under vacuum. The crude diketone of formula II is dissolved in 95% ethanol (900 ml) and treated at 0° C. with 98% hydrazine hydrate (4 moles). The mixture is stirred for 3 hours at room temperature and water (200 ml) is added. Most of the solvent is distilled under vacuum and the product is extracted with methylene chloride, washed with water, dried over sodium sulphate and evaporated to dryness in vacuo. The crude product of the title crystallizes from ethyl acetate. M.p. 163°–165° C.

Following essentially the same procedure, the compounds of the Examples 2 to 16 are obtained:

EXAMPLE 2:
5-acetyl-3-phenyl-4,5,6,7-tetrahydro-1H-pyrazolo/4,3-c/pyridine

M.p. 223°–225° C. (methanol)

EXAMPLE 3:
5-acetyl-3-(4-chlorophenyl)-4,5,6,7-tetrahydro-1H-pyrazolo/4,3-c/pyridine M.p. 215°–217° C. (ethyl acetate)

EXAMPLE 4:
5-acetyl-3-(4-nitrophenyl)-4,5,6,7-tetrahydro-1H-pyrazolo/4,3-c/pyridine M.p. 215°–217° C. (methanol/methylene chloride)

EXAMPLE 5:
5-acetyl-3-(4-methoxyphenyl)-4,5,6,7-tetrahydro-1H-pyrazolo/4,3-c/pyridine M.p. 176°–177° C. (ethyl acetate)

EXAMPLE 6:
5-acetyl-3-(4-methylphenyl)-4,5,6,7-tetrahydro-1H-pyrazolo/4,3-c/pyridine M.p. 168°–178° C. (ethyl acetate/methylene chloride)

EXAMPLE 7:
5-acetyl-3-(2-fluorophenyl)-4,5,6,7-tetrahydro-1H-pyrazolo/4,3-c/pyridine M.p. 171°–172° C. (ethyl acetate)

EXAMPLE 8:
5-acetyl-3-(3-chlorophenyl)-4,5,6,7-tetrahydro-1H-pyrazolo/4,3-c/pyridine M.p. 187°–189° C. (ethyl acetate/methanol)

EXAMPLE 9:
5-acetyl-3-(3-fluorophenyl)-4,5,6,7-tetrahydro-1H-pyrazolo/4,3-c/pyridine M.p. 204°–206° C. (ethyl acetate/methanol)

EXAMPLE 10:
5-acetyl-3-(4-cyanophenyl)-4,5,6,7-tetrahydro-1H-pyrazolo/4,3-c/pyridine M.p. 252°–254° C. (ethanol/methylene chloride)

EXAMPLE 11:
5-acetyl-3-(2-furanyl)-4,5,6,7-tetrahydro-1H-pyrazolo/4,3-c/pyridine M.p. 185° C. (dec) (ethyl acetate)

EXAMPLE 12:
5-acetyl-3-(2-thienyl)-4,5,6,7-tetrahydro-1H-pyrazolo/4,3-c/pyridine M.p. 208°–209° C. (ethanol/methylene chloride)

EXAMPLE 13:
5-acetyl-3-(3-trifluoromethyl-phenyl)-4,5,6,7-tetrahydro-1H-pyrazolo/4,3-c/pyridine M.p. 178°–179° C. (ethyl acetate)

EXAMPLE 14:
5-acetyl-3-(3,4-dimethoxyphenyl)-4,5,6,7-tetrahydro-1H-pyrazolo/4,3-c/pyridine M.p. 159°–160° C. (ethyl acetate)

EXAMPLE 15:
5-acetyl-3-(4-ethoxyphenyl)-4,5,6,7-tetrahydro-1H-pyrazolo/4,3-c/pyridine M.p. 181°–182° C. (ethyl acetate)

EXAMPLE 16:
5-acetyl-3-(4-methylthiophenyl)-4,5,6,7-tetrahydro-1H-pyrazolo/4,3-c/pyridine

EXAMPLE 17:
5-Benzoyl-3-(4-fluorophenyl)-4,5,6,7-tetrahydro-1H-pyrazolo/4,3-c/pyridine N-Benzoyl-4-piperidone (0,2 mole) and morpholine (0,22 mole) in benzene (83 ml) are treated with 10 mg of p.toluensulfonic acid and refluxed for 8 hours in a Marcusson apparatus. The solvent is removed under reduced pressure and the residue is taken up with anhydrous methylene chloride (200 ml). Triethylamine (0,22 mole) is added and, then, p-fluorobenzoylchloride (0,22 mole) dissolved in methylene chloride (40 ml) is dropped into the reaction flask, keeping the temperature at about 0° C.+5° C. The reaction mixture is left at room temperature under stirring for 20 hours. Subsequently, 5% hydrochloric acid (255 ml) is added at 10° C. and stirring is continued for 30 minutes. The organic layer is separated, washed twice with water, dried over sodium sulfate, and evaporated under vacuum. The crude diketone of formula II is then dissolved in ethanol (240 ml), and added dropwise with 98% hydrazine hydrate (38.8 ml; 0.8 mole). The temperature is kept around 10° to 15°. After stirring for 3.5 hours at 20° C. the reaction mixture is added with water (100 ml) and the ethanol is evaporated under reduced pressure; the aqueous layer is then extracted with methylene chloride, the organic layer washed with water, dried, and the solvent evaporated under reduced pressure. The residue is crystallized from ethyl acetate. Other product of the title was obtained after chromatography of the mother liquors on a silica gel column, eluting with methylene chloride/ethyl acetate, 7:3 and evaporating the solvent of the pooled fractions.
M.p. 159°–160° C.

EXAMPLE 18:
5-Benzoyl-3-phenyl-4,5,6,7-tetrahydro-1H-pyrazolo/4,4-c/pyridine It is obtained following essentially the above procedure, but employing benzoylchloride instead of p-fluorobenzoylchloride. M.p. 197°–198° C. (ethyl acetate)

EXAMPLE 19:
3-(4-fluorophenyl)-4,5,6,7-tetrahydro-1H-pyrazolo/4,3-c/pyridine A mixture of the compound of Example 1, (20 g; 0,077 mole) in 10% hydrochloric acid (200 ml) is refluxed for 2 hours, filtered hot and the filtrate concentrated to 50 ml. The chilled solution is treated with an excess of 15% aqueous sodium hydroxide and the desired product is collected and thoroughly washed with water. The compound of the title is crystallized from an ethanol-water mixture. M.p. 225°–227° C.

The following examples 20 to 28 are prepared essentially following the procedure of Example 19.

EXAMPLE 20:
3-(4-methoxyphenyl)-4,5,6,7-tetrahydro-1H-pyrazolo/4,3-c/pyridine M.p. 220°–222° C. (benzene-ethanol)

EXAMPLE 21:
3-(2-fluorophenyl)-4,5,6,7-tetrahydro-1H-pyrazolo/4,3-c/pyridine M.p. 252°–253° C. (methanol)

EXAMPLE 22:
3-(3-chlorophenyl)-4,5,6,7-tetrahydro-1H-pyrazolo/4,3-c/pyridine M.p. 240°–242° C. (methanol)

EXAMPLE 23:
3-(3-fluorophenyl)-4,5,6,7-tetrahydro-1H-pyrazolo/4,3-c/pyridine M.p. 241°–243° C. (ethanol-methylene chloride)

EXAMPLE 24:
3-(4-cyanophenyl)-4,5,6,7-tetrahydro-1H-pyrazolo/4,3-c/pyridine

M.p. 224°–225° C. (ethanol-methylene chloride)

EXAMPLE 25:
3-(3-trifluoromethylphenyl)-4,5,6,7-tetrahydro-1H-pyrazolo/4,3-c/pyridine M.p. 165°–166° C. (ethyl acetate)

EXAMPLE 26:
3-(3,4-dimethoxyphenyl)-4,5,6,7-tetrahydro-1H-pyrazolo/4,3-c/pyridine M.p. 254°–255° C. (methanol)

EXAMPLE 27:
3-(4-ethoxyphenyl)-4,5,6,7-tetrahydro-1H-pyrazolo/4,3-c/pyridine M.p. 192°–194° C. (ethanol)

EXAMPLE 28:
3-(4-methylthiophenyl)-4,5,6,7-tetrahydro-1H-pyrazolo/4,3-c/pyridine The following hydrochlorides described in Examples 29 to 32 are obtained essentially following the procedure of Example 19 simply concentrating and cooling the reaction mixture without adding the basic solution.

EXAMPLE 29:
3-phenyl-4,5,6,7-tetrahydro-1H-pyrazolo/4,3-c/pyridine, dihydrochloride M.p. 248 (dec.) (methanol-ethyl ether)

EXAMPLE 30:
3-(4-nitrophenyl)-4,5,6,7-tetrahydro-1H-pyrazolo/4,3-c/pyridine, hydrochloride M.p. 282° C. (methanol-methylene chloride)

EXAMPLE 31:
3-(4-chlorophenyl)-4,5,6,7-tetrahydro-1H-pyrazolo/4,3-c/pyridine, hydrochloride M.p. 272°–274° C. (methanol)

EXAMPLE 32:
3-(4-methylphenyl)-4,5,6,7-tetrahydro-1H-pyrazolo/4,3-c/pyridine, dihydrochloride M.p. 257°–260° C. (methanol-ethyl ether)

The methansulfonates described in the following examples 33 and 34 are obtained adding a molar amount of a solution of methanesulfonic acid in ethanol to a hot ethanol solution of the corresponding free base, obtained essentially following the above outlined process (see Example 19).

EXAMPLE 33:
3-(2-furyl)-4,5,6,7-tetrahydro-1H-pyrazolo/4,3-c/pyridine, methansulfonate M.p. 194°–195° C. (ethanol)

EXAMPLE 34:
3-(2-thienyl)-4,5,6,7-tetrahydro-1H-pyrazolo/4,3-c/pyridine, methanesulfonate M.p. 219°–221° C. (ethanol)

EXAMPLE 35:
3-(3,4-dihydroxyphenyl)-4,5,6,7-tetrahydro-1H-pyrazolo/4,3-c/pyridine hydrobromide, methansulfonate A mixture of the compound of Example 14 /5-acetyl-3-(3,4-dimethoxyphenyl)-4,5,6,7-tetrahydro-1H-pyrazolo-/4,3-c/pyridine/ (10 g; 0,033 mole) in acetic acid (100 ml) and 48% hydrobromic acid (100 ml) is refluxed for 5 hours. After cooling, the crystalline dihydrobromide of the product of the title is collected. The corresponding monohydrobromide is obtained adding to the above product a molar amount of ethanolic triethylamine. A hot solution of the monohydrobromide in methanol is treated with a molar amount of methanolic methanesulfonic acid, the mixture is cooled and the product of the title is collected.

M.p. 207°–209° C. (methanol)

EXAMPLE 36:
5-methyl-3-phenyl-4,5,6,7-tetrahydro-1H-pyrazolo/4,3-c/pyridine, citrate A mixture of the compound of Example 29 /3-phenyl-4,5,6,7-tetrahydro-1H-pyrazolo/4,3-c/pyridine, (5.1 g; 0.0179 mole), 99% formic acid (55 ml) and 40% aqueous formaldehyde (5.5 ml) is heated on a steam bath for 3 hours. The solvent is distilled off in vacuo. The residue is alkalinized with saturated sodium carbonate aqueous solution and extracted with methylene chloride. The organic layer is washed, dried, and the solvent is evaporated. The obtained solid residue, i.e. the crude base, is dissolved in hot ethanol and treated with an equimolar amount of citric acid dissolved in ethanol. After stripping the solvent off, the salt is crystallized from methanol. M.p. 194°–195° C.

The compounds of examples 37 to 40, are prepared essentially following the above procedure, starting from the corresponding compound of formula I wherein R is hydrogen.

EXAMPLE 37:
3-(4-chlorophenyl)-5-methyl-4,5,6,7-tetrahydro-1H-pyrazolo/4,3-c/pyridine, citrate M.p. 198°–200° C. (ethanol-ethyl ether)

EXAMPLE 38:
3-(4-fluorophenyl)-5-methyl-4,5,6,7-tetrahydro-1H-pyrazolo/4,3-c/pyridine M.p. 198°–200° C. (ethyl acetate)

The maleic acid addition salt of the foregoing compound is prepared by adding it with a slight molar excess of maleic acid, employing ethanol as the reaction solvent and recovering as known in the art:
3-(4-fluorophenyl)-5-methyl-4,5,6,7-tetrahydro-1H-pyrazolo/4,3-c/pyridine, maleate
M.p. 174°–175° C.

EXAMPLE 39:
5-methyl-3-(4-methylphenyl)-4,5,6,7-tetrahydro-1H-pyrazolo/4,3-c/pyridine M.p. 205°–208° C. (ethanol)

EXAMPLE 40:
5-methyl-3-(3-trifluoromethylphenyl)-4,5,6,7-tetrahydro-1H-pyrazolo/4,3-c/pyridine M.p. 143°–144° C. (ethyl ether)

EXAMPLE 41:
5-ethyl-3-(4-fluorophenyl)-4,5,6,7-tetrahydro-1H-pyrazolo/4,3-c/pyridine, malonate To a cooled suspension of lithium aluminum hydride (4.5 g) in dry tetrahydrofuran (200 ml) a suspension of the compound of the Example 1 (7.8 g) in tetrahydrofuran (150 ml) is added and slowly heated to reflux temperature. After about 3 hours, the reaction mixture is worked up to yield the crude product of the title which is purified by column chromatography using silica gel (240 g) and carrying out the elution with a 5% mixture of methanol in chloroform. The free base is solidified with ether and transformed into the corresponding malonic acid salt, adding to the free base an equimolecular amount of malonic acid in ethanol. After dilution with ethyl ether, the compound of the title is obtained. M.p. 165°–167° C. (ethenol/ethyl ether).

Similarly, the following compounds of examples 42, 43, and 44, were obtained starting from the suitable derivative of formula I wherein $R^1$ and Ar are defined as above, and R is acetyl.

EXAMPLE 42:
5-ethyl-3-phenyl-4,5,6,7-tetrahydro-1H-pyrazolo/4,3-c/pyridine, hydrochloride M.p. 260°–263° C. (methanol/ethyl ether)

EXAMPLE 43:
5-ethyl-3-(4-methoxyphenyl)-4,5,6,7-tetrahydro-1H-pyrazolo/4,3-c/pyridine M.p. 143°–144° C. (ethyl ether)

EXAMPLE 44:
5-ethyl-3-(4-methylphenyl)-4,5,6,7-tetrahydro-1H-pyrazolo/4,3-c/pyridine malonate M.p. 147°–148° C. (ethanol/ethyl ether)

EXAMPLE 45:

5-(2-methylethyl)-4-thienyl-4,5,6,7-tetrahydro-1H-pyrazolo/4,3-c/pyridine-4,5,6,7-tetrahydro-/4,3-c/pyridine (the compound of Example 34) (10.12 g; 0,05 mole), potassium iodide (8.3 g; 0.05 mole), potassium carbonate (27.6 g; 0.2 mole), 2-bromopropane (5.16 ml; 0.055 mole) in methylethylketone (300 ml) is refluxed for about 16 hours. The solvent is then evaporated and the residue is taken up with water and extracted with methylene chloride. The organic phase is subsequently washed with water dried and concentrated. The residue is purified through a silica gel column using methylene chloride with increasing amount of methanol as the eluting system, yielding the compound of the title, after concentration of the pooled fractions (ethyl ether). M.p. 130°–131° C.

EXAMPLE 46:

5-acetyl-3-(3-fluorophenyl)-4,5,6,7-tetrahydro-1-methyl-1H-pyrazolo/4,3-c/pyridine To a stirred solution of 5-acetyl-3-(3-fluorophenyl)-4,5,6,7-tetrahydro-1H-pyrazolo/4,3-c/pyridine (the compound of Example 9) (27 g; 0,104 mole) in anhydrous dimethylformamide (270 ml) 55% sodium hydride in mineral oil (5.24 g) is added portionwise at about 10° C. The temperature is kept at 50° C. for 30 minutes and subsequently lowered to 20° C. A solution of methyl iodide (8 ml) in dimethylformamide (30 ml) is added dropwise to the reaction mixture and stirring is continued for 3 hours. After adding a few drops of methanol, the solvent is taken off in vacuo and the reaction mixture is poured in diluted ice-cold water and extracted with methylene chloride. The organic layer is washed with water, dried over sodium sulfate, and the solvent is evaporated under reduction pressure. The oily residue is triturated with ethyl ether and collected. A further amount of product is obtained from the chromatography of the mother liquor on a silica gel column (300 g), eluting with 1% methanol-methylene chloride. M.p. 158°–159° C. (ethyl acetate)

EXAMPLES 47 TO 54

The following compounds are obtained following essentially the procedure set forth in the above Example 46 starting from the corresponding compounds of formula I, wherein $R^1$ and Ar are defined as above and R is an acetyl or a benzoyl group.

EXAMPLE 47:

5-acethyl-3-phenyl-4,5,6,7-tetrahydro-1-methyl-1H-pyrazolo/4,3-c/pyridine

M.p. 173°–174° C. (ethyl acetate)

EXAMPLE 48:

5-acetyl-3-(4-chlorophenyl)-4,5,6,7-tetrahydro-1-methyl-1H-pyrazolo/4,3-c/pyridine M.p. 185°–186° C. (ethyl acetate)

EXAMPLE 49:

5-acetyl-3-(4-fluorophenyl)-4,5,6,7-tetrahydro-1-methyl-1H-pyrazolo/4,3-c/pyridine M.p. 163°–166° C. (ethyl acetate)

EXAMPLE 50:

5-acethyl-3-(2-fluorophenyl)-4,5,6,7-tetrahydro-1-methyl-1H-pyrazolo/4,3-c/pyridine M.p. 118°–119° C. (ethyl acetate)

EXAMPLE 51:

5-acetyl-3-(3-chlorophenyl)-4,5,6,7-tetrahydro-1-methyl-1H-pyrazolo/4,3-c/pyridine M.p. 145°–147° C. (ethyl acetate)

EXAMPLE 52:

5-acetyl-3-(2-furanyl)-4,5,6,7-tetrahydro-1-methyl-1H-pyrazolo/4,3-c/pyridine

M.p. 141°–142° C. (ethyl acetate)

EXAMPLE 53:

5-benzoyl-3-phenyl-4,5,6,7-tetrahydro-1-methyl-1H-pyrazolo/4,3-c/pyridine

M.p. 200°–202° C. (ethyl acetate)

EXAMPLE 54:

5-benzoyl-3-(4-fluorophenyl)-4,5,6,7-tetrahydro-1-methyl-1H-pyrazolo/4,3-c/pyridine M.p. 186°–187° C. (ethyl acetate)

The following compounds of Examples 55 to 58 are prepared following essentially the procedure set forth in Example 46, starting from the compounds of Example 1, 12, or 17, respectively, and employing ethyl bromide at 40° C. as the alkylating agent.

EXAMPLE 55:

5-acetyl-3-(4-fluorophenyl)-4,5,6,7-tetrahydro-1-ethyl-1H-pyrazolo/4,3-c/pyridine M.p. 140°–141° C. (ethyl acetate)

EXAMPLE 56:

5-acetyl-3-3(2-thienyl)-4,5,6,7-tetrahydro-1-ethyl-1H-pyrazolo/4,3-c/pyridine

M.p. 150°–151° C. (ethyl acetate)

EXAMPLE 57:

5-benzoyl-3-(4-fluorophenyl)-4,5,6,7-tetrahydro-1-ethyl-1H-pyrazolo/4,3-c/pyridine M.p. 155°–156° C. (ethyl acetate)

EXAMPLE 58:

5-benzoyl-3-(4-fluorophenyl)-4,5,6,7-tetrahydro-2-ethyl-2H-pyrazolo/4,3-c/pyridine M.p. 139°–140° C. (ethyl ether)

The compounds of Examples 59 to 62 are obtained according to a procedure similar to that of Example 46, starting from the compound of Example 1, 2, 11 or 18 respectively, and using 2-bromopropane at 50° C. for 5 hours as the alkylating agent.

EXAMPLE 59:

5-acetyl-3-(4-fluorophenyl)-4,5,6,7-tetrahydro-1-(2-methylethyl)-1H-pyrazolo/4,3-c/pyridine M.p. 146°–147° C. (ethyl acetate)

EXAMPLE 60:

5-acetyl-3-phenyl-4,5,6,7-tetrahydro-1-(2-methylethyl)-1H-pyrazolo/4,3-c/pyridine M.p. 134°–135° C. (ethyl ether)

EXAMPLE 61:

5-acetyl-3-3(2-furanyl)-4,5,6,7-tetrahydro-1H-(2-methylethyl)-1H-pyrazolo/4,3-c/pyridine M.p. 134°–135° C. (ethyl acetate/ethyl ether)

EXAMPLE 62:
5-benzoyl-3-phenyl-4,5,6,7-tetrahydro-1-(2-methylethyl)-1H-pyrazolo/4,3-c/pyridine M.p. 171°–172° C. (ethyl acetate)

The compounds of Examples 63 to 66 are obtained essentially following the process of Example 46, starting from the compound of Example 1 and using respectively 1-bromopropane, 1-bromobutane, 1-bromopentane or 1-bromoexane as the alkylating agent.

EXAMPLE 63:
5-acetyl-3-(4-fluorophenyl)-4,5,6,7-tetrahydro-1-n.propyl-1H-pyrazolo/4,3-c/pyridine M.p. 130°–131° C. (ethyl acetate)

EXAMPLE 64:
5-acetyl-3-(4-fluorophenyl)-4,5,6,7-tetrahydro-1-n.butyl-1H-pyrazolo/4,3-c/pyridine M.p. 119°–121° C. (ethyl acetate)

EXAMPLE 65:
5-acetyl-3-(4-fluorophenyl)-4,5,6,7-tetrahydro-1-n.pentyl-1H-pyrazolo/4,3-c/pyridine M.p. 86°–87° C. (ethyl ether)

EXAMPLE 66:
5-acetyl-3-(4-fluorophenyl)-4,5,6,7-tetrahydro-1-n.hexyl-1H-pyrazolo/4,3-c/pyridine M.p. 66°–67° C. (ethyl ether).

The compounds of Examples 67 to 84 are prepared according to a procedure similar to that described in Example 46, starting from the compound of Example 1, and using the appropriate phenyl($C_1$-$C_6$)alkyl chloride derivative as the alkylating agent. The alkylating step was carried out at about 50° C. for about 3 hours.

EXAMPLE 67:
5-acetyl-3-(4-fluorophenyl)-4,5,6,7-tetrahydro-1-phenylmethyl-1H-pyrazolo/(4,3-c/pyridine M.p. 150°–151° C. (ethyl acetate)

EXAMPLE 68:
5-acetyl-3-(4-fluorophenyl)-4,5,6,7-tetrahydro-1-(4-chlorophenylmethyl)-1H-pyrazolo-/4,3-c/pyridine M.p. 159°–160° C. (ethyl acetate)

EXAMPLE 69:
5-acetyl-3-(4-fluorophenyl)-4,5,6,7-tetrahydro-1-(4-methoxyphenylmethyl)-1H-pyrazolo-/4,3-c/pyridine M.p. 147°–148° C. (ethyl acetate)

EXAMPLE 70:
5-acetyl-3-(4-fluorophenyl)-4,5,6,7-tetrahydro-1-(4-fluorophenylmethyl)-1H-pyrazolo-/4,3-c/pyridine M.p. 136°–137° C. (ethyl acetate)

EXAMPLE 71:
5-acetyl-3-(4-fluorophenyl)-4,5,6,7-tetrahydro-1-(4-methylphenylmethyl)-1H-pyrazolo-/4,3-c/pyridine M.p. 163°–164° C. (ethyl acetate)

EXAMPLE 72:
5-acetyl-3-(4-fluorophenyl)-4,5,6,7-tetrahydro-1-(3,4-dichlorophenylmethyl)-1H-pyrazolo-/4,3-c/pyridine M.p. 184°–185° C. (ethyl acetate)

EXAMPLE 73:
5-acetyl-3-(4-fluorophenyl)-4,5,6,7-tetrahydro-1-(2-phenyl ethyl)-1H-pyrazolo/4,3-c/pyridine M.p. 154°–155° C. (ethyl acetate)

EXAMPLE 74:
5-acetyl-3-(4-fluorophenyl)-4,5,6,7-tetrahydro-1-(3-phenyl propyl)-1H-pyrazolo/4,3-c/pyridine M.p. 107°–108° C. (ethyl acetate)

EXAMPLE 75:
5-acetyl-1-(2-chlorophenylmethyl)-3-(4-fluorophenyl)-4,5,6,7-tetrahydro-1H-pyrazolo/4,3-c/pyridine M.p. 156°–157° C. (ethyl acetate-ethyl ether)

EXAMPLE 76:
5-acetyl-3-(3-trifluoromethylphenyl)-4,5,6,7-tetrahydro-1-phenylmethyl-1H-pyrazolo-/4,3-c/pyridine M.p. 170°–171° C. (ethyl acetate)

EXAMPLE 77:
5-acetyl-3-(4-fluorophenyl)-4,5,6,7-tetrahydro-1-(2-phenylethyl)-1H-pyrazolo/4,3-c/pyridine M.p. 160°–161° C. (ethyl acetate)

EXAMPLE 78:
5-acetyl-(1-cyclopropylcarbonyl phenyl)-4,5,6,7-tetrahydro-1H-pyrazolo/4,3-c/pyridine M.p. 190°–191° C. (ethyl ether)

EXAMPLE 79:
5-acetyl-4,5,6,7-tetrahydro-3-phenyl-1-phenylmethyl-1H-pyrazolo/4,3-c/pyridine M.p. 172°–173° C. (ethyl ether)

EXAMPLE 80:
5-acetyl-3-(4-chlorophenyl)-4,5,6,7-tetrahydro-1-phenylmethyl-1H-pyrazolo/4,3-c/pyridine M.p. 188°–189° C. (ethyl acetate methylene chloride)

EXAMPLE 81:
5-acetyl-4,5,6,7-tetrahydro-3-(4-methylphenyl)-1-phenylmethyl-1H-pyrazolo/4,3-c/pyridine M.p. 170°–171° C. (ethyl acetate methylene chloride)

Essentially following the procedure of Example 42, starting from the compound of Example 1 and using 1-bromo-2-(N-methyl-2-pyrrolidinyl)ethylene as the alkylating agent the following compound is obtained:

EXAMPLE 82:
5-acetyl-3-(4-fluorophenyl)-4,5,6,7-tetrahydro-1/2-(N-methyl-2-pyrrolidinyl)ethyl/1H-pyrazolo/4,3-c/pyridine M.p. 105°–106° C. (ethyl ether)

EXAMPLE 83:
5-acetyl-3-(4-ethoxyphenyl)-1-(phenylmethyl)-4,5,6,7-tetrahydro-1H-pyrazolo/4,3-c/pyridine M.p. 174°–176° C. (ethyl acetate)

EXAMPLE 84:
5-acetyl-3(4-methylthiophenyl)-1-phenylmethyl-4,5,6,7-tetrahydro-1H-pyrazolo/4,3-c/pyridine

EXAMPLE 85:
5-acetyl-1-(4-acetoxyphenylmethyl)-3(4-fluorophenyl)-4,5,6,7-tetrahydro-1H-pyrazolo/4,3-c/pyridine

EXAMPLE 86:
5-acetyl-3-(2-thienyl)-4,5,6,7-tetrahydro-1-phenylmethyl-1H-pyrazolo/4,3-c/pyridine (It is obtained following essentially the procedure of Example 46 starting from 5-acetyl-3-(2-thienyl)-4,5,6,7-tetrahydro-1H-pyrazolo/4,3-c/pyridine and using benzyl chloride as the alkylating agent). M.p. 184°–185° C. (ethyl acetate

EXAMPLE 87:
5-acetyl-1,3-di-(4-fluorophenyl)-4,5,6,7-tetrahydro-1H-pyrazolo/4,3-c/pyridine A mixture of 5-acetyl-3-(4-fluorophenyl)-4,5,6,7-tetrahydro-1H-pyrazolo/4,3-c/pyridine (20,72 g), 4-bromofluorobenzene (29.64 ml), cuprous bromide (14.4 g) and sodium carbonate (9.33 g) is heated at 200° C. for 14 hours under a nitrogen atmosphere. After cooling, the reaction mixture is poured into 216 ml of water and 44 ml of ethylenediamine. Ethyl acetate (400 ml) is then added and the resulting mixture is extracted several times with ethyl acetate and the combined extracts are washed with water, dried and evaporated to give an oily product. Chromatography of the oil on silica gel (eluting with chloroform-methanol 98:2) gives the compound of the title. M.p. 191°–192° C. (ethyl acetate).

EXAMPLE 88:
5-acetyl-3-(4-fluorophenyl)-1-(4-nitrophenylmethyl)-4,5,6,7-tetrahydro-1H-pyrazolo/4,3-c/pyridine A mixture of the compound of Example 1 (7.77 g), 4-nitrobenzyl chloride (5.4 g), potassium carbonate (12.45 g) and potassium iodide (0.51 g) in dry methyl ethyl ketone (120 ml) is refluxed for 8 hours. After evaporation of the solvent, the residue is treated with water and methylene chloride. The organic layer is washed with water, dried and evaporated to give the crude solid product of the title which crystallizes from ethyl acetate. M.p. 193°–5° C.

EXAMPLE 89:
5-acetyl-3-(4-fluorophenyl)-4,5,6,7-tetrahydro-1(2)phenyl-1(2)H-pyrazolo/4,3-c/pyridine Crude N-acetyl-3-/(4-fluorophenyl)carbonyl/-4-piperidone (0.3 mole) dissolved in ethanol (270 ml) is treated with phenylhydrazine (0.6 mole) at 0° C., under stirring. After 3 hours at room temperature, the resulting thick slurry is diluted with 50 ml water, cooled, collected and washed with water. The crude compound of the title is isolated and used as such.

The compound of Example 90 to 127 are obtained from the corresponding derivatives of formula I, wherein Ar is as above defined, $R^1$ is as above and different from hydrogen, and R is acetyl or benzoyl, as the case may be prepared essentially following the procedure set forth in Example 19.

EXAMPLE 90:
3-(4-fluorophenyl)-1-methyl-4,5,6,7-tetrahydro-1H-pyrazolo/4,3-c/pyridine M.p. 119°–121° C. (water)

EXAMPLE 91:
3-(2-fluorophenyl)-1-methyl-4,5,6,7-tetrahydro-1H-pyrazolo/4,3-c/pyridine, methanesulfonate M.p. 196°–197° C. (ethanol-ethyl ether)

EXAMPLE 92:
3-(3-chlorophenyl)-1-methyl-4,5,6,7-tetrahydro-1H-pyrazolo/4,3-c/pyridine M.p. 123°–124° C. (ethyl acetate)

EXAMPLE 93:
3-(3-fluorophenyl)-1-methyl-4,5,6,7-tetrahydro-1H-pyrazolo/4,3-c/pyridine M.p. 104°–105° C. (ethyl ether)

EXAMPLE 94:
1-ethyl-3-(4-fluorophenyl)-4,5,6,7-tetrahydro-1H-pyrazolo/4,3-c/pyridine, methanesulfonate M.p. 220°–221° C. (ethanol)

EXAMPLE 95:
3-(4-fluorophenyl)-1-(2-methylethyl)-4,5,6,7-tetrahydro-1H-pyrazolo/4,3-c/pyridine, methanesulfonate M.p. 244°–245° C. (ethanol)

EXAMPLE 96:
1-methyl-3-phenyl-4,5,6,7-tetrahydro-1H-pyrazolo/4,3-c/pyridine, methanesulfonate M.p. 240°–242° C. (ethanol)

EXAMPLE 97:
1-(2-methylethyl)-3-phenyl-4,5,6,7-tetrahydro-1H-pyrazolo/4,3-c/pyridine M.p. 102°–103° C. (ethyl ether-hexane)

EXAMPLE 98:
3-(2-furanyl)-1-(1-methylethyl)-4,5,6,7-tetrahydro-1H-pyrazolo/4,3-c/pyridine, methanesulfonate sulfonate M.p. 206°–207° C. (ethanol)

EXAMPLE 99:
3-(2-furanyl)-1-methyl-4,5,6,7-tetrahydro-1H-pyrazolo/4,3-c/pyridine, methanesulfonate M.p. 201°–203° C. (ethanol)

EXAMPLE 100:
3-(4-fluorophenyl)-1-phenylmethyl-4,5,6,7-tetrahydro-1H-pyrazolo/4,3-c/pyridine, hydrochloride M.p. 286°–289° C. (methanol)

EXAMPLE 101:
3-(4-fluorophenyl)-1-phenyl-4,5,6,7-tetrahydro-1H-pyrazolo/4,3-c/pyridine, methanesulfonate M.p. 197°–198° C. (ethyl acetate-methanol)

EXAMPLE 102:
1-ethyl-3-(2-thienyl)-4,5,6,7-tetrahydro-1H-pyrazolo/4,3-c/pyridine, methanesulfonate M.p. 185°–186° C. (ethanol)

EXAMPLE 103:
1-(4-chlorophenylmethyl)-3-(4-fluorophenyl)-4,5,6,7-tetrahydro-1H-pyrazolo/4,3-c/pyridine, hydrochloride M.p. 255° C. (ethanol)

EXAMPLE 104:
3-(4-chlorophenyl)-1-methyl-4,5,6,7-tetrahydro-1H-pyrazolo/4,3-c/pyridine, hydrochloride M.p. 320°–322° C. (water)

EXAMPLE 105:
3-(4-fluorophenyl)-1-(4-methoxyphenylmethyl)-4,5,6,7-tetrahydro-1H-pyrazolo/4,3-c/pyridine, hydrochloride M.p. 216°–218° C. (methanol-ethyl ether)

EXAMPLE 106:
3-(4-fluorophenyl)-1-(4-fluorophenyl)methyl)-4,5,6,7-tetrahydro-1H-pyrazolo/4,3-c/pyridine M.p. 82°–83° C. (ethyl ether)

EXAMPLE 107:
3-(4-fluorophenyl)-1-(4-methylphenylmethyl)-4,5,6,7-tetrahydro-1H-pyrazolo/4,3-c/pyridine, methanesulfonate

EXAMPLE 108:
1-(3,4-dichlorophenylmethyl)-3-(4-fluorophenyl)-4,5,6,7-tetrahydro-1H-pyrazolo/4,3-c/pyridine, hydrochloride M.p. 275°–276° C. (methanol)

EXAMPLE 109:
1-phenylmethyl-3-(2-thienyl)-4,5,6,7-tetrahydro-1H-pyrazolo/4,3-c/pyridine, hydrochloride M.p. 284°–285° C. (methanol)

EXAMPLE 110:
3-(4-fluorophenyl)-1-(2-phenylethyl)-4,5,6,7-tetrahydro-1H-pyrazolo/4,3-c/pyridine, methanesulfonate M.p. 244°–246° C. (ethanol)

EXAMPLE 111:
3-(4-fluorophenyl)-1-(3-phenylpropyl)-4,5,6,7-tetrahydro-1H-pyrazolo/4,3-c/pyridine, methanesulfonate M.p. 209°–211° C. (ethanol)

EXAMPLE 112:
3-(4-fluorophenyl)-1-n.propyl-4,5,6,7-tetrahydro-1H-pyrazolo/4,3-c/pyridine, methanesulfonate M.p. 220°–222° C. (ethanol-ethyl ether)

EXAMPLE 113:
3-(4-fluorophenyl)-1-n.butyl-4,5,6,7-tetrahydro-1H-pyrazolo/4,3-c/pyridine, methanesulfonate M.p. 224°–225° C. (ethanol-ethyl ether)

EXAMPLE 114:
1-(2-chlorophenylmethyl)-3-(4-fluorophenyl)-4,5,6,7-tetrahydro-1H-pyrazolo/4,3-c/pyridine, methanesulfonate M.p. 221°–223° C. (ethanol-ethyl ether)

EXAMPLE 115:
3-(3-trifluoromethylphenyl)-4,5,6,7-tetrahydro-1-phenylmethyl-1H-pyrazolo/4,3-c/pyridine, methanesulfonate M.p. 192°–193° C. (ethanol)

EXAMPLE 116:
3-(4-fluorophenyl)-4,5,6,7-tetrahydro-1-(1-phenylethyl)-1H-pyrazolo/4,3-c/pyridine, methanesulfonate M.p. 225°–226° C. (ethanol)

EXAMPLE 117:
4,5,6,7-tetrahydro-3-phenyl-1-phenylmethyl-1H-pyrazolo/4,3-c/pyridine, hydrochloride M.p. 283°–284° C. (ethanol-water)

EXAMPLE 118:
3-(4-chlorophenyl)-4,5,6,7-tetrahydro-1-phenylmethyl-1H-pyrazolo/4,3-c/pyridine, hydrochloride M.p. 277°–278° C. (ethanol-water)

EXAMPLE 119:
4,5,6,7-tetrahydro-3-(4-methylphenyl)-1-phenylmethyl-1H-pyrazolo/4,3-c/pyridine, hydrochloride M.p. 291°–293° C. (methanol)

EXAMPLE 120:
3-(4-fluorophenyl)-4,5,6,7-tetrahydro-1-/2-(N-methyl-2-pyrrolidinyl)ethyl/-1H-pyrazolo/4,3-c/pyridine M.p. 68°–69° C. (n-hexane)

EXAMPLE 121:
1,3-di(4-fluorophenyl)-4,5,6,7-tetrahydro-1H-pyrazolo/4,3-c/pyridine, hydrochloride M.p. 293°–295° C. (ethanol)

EXAMPLE 122:
3-(4-fluorophenyl)-4,5,6,7-tetrahydro-1-n.pentyl-1H-pyrazolo/4,3-c/pyridine, methanesulfonate M.p. 220°–222° C. (ethanol)

EXAMPLE 123:
3-(4-fluorophenyl)-4,5,6,7-tetrahydro-1-n.hexyl-1H-pyrazolo/4,3-c/pyridine, methanesulfonate M.p. 214°–215° C. (ethanol)

EXAMPLE 124:
3-(4-ethoxyphenyl)-1-phenylmethyl-4,5,6,7-tetrahydro-1H-pyrazolo/4,3-c/pyridine, hydrochloride M.p. 291°–293° C. (methanol)

EXAMPLE 125:
3-(4-fluorophenyl)-1-(4-nitrophenylmethyl)-4,5,6,7-tetrahydro-1H-pyrazolo/4,3-c/pyridine, hydrochloride M.p. 281°–283° C. (ethanol)

EXAMPLE 126:
3-(4-methylthiophenyl)-1-phenylmethyl-4,5,6,7-tetrahydro-1H-pyrazolo/4,3-c/pyridine

EXAMPLE 127:
3-(4-fluorophenyl)-1-(4-hydroxyphenylmethyl)-4,5,6,7-tetrahydro-1H-pyrazolo/4,3-c/pyridine, hydrochloride

EXAMPLE 128:
3-(4-fluorophenyl)-5-methyl-1-phenylmethyl-4,5,6,7-tetrahydro-1H-pyrazolo/4,3-c/pyridine, methanesulfonate A mixture of 3-(4-fluorophenyl)-1-phenylmethyl-4,5,6,7-tetrahydro-1H-pyrazolo/4,3-c/pyridine (5.5 g; 0.0179 mole), 99% formic acid (55 ml) and 40% aqueous formaldehyde (5.5 ml) is heated on a steam both for 3 hours. The solvent is distilled off in vacuo; the residue is made alkaline with saturated sodium carbonate water solution and extracted with methylene chloride. The organic layer is washed, dried, and evaporated. The obtained solid residue, i.e. crude base, is dissolved in hot ethanol and treated with an equimolar amount of methanesulfonate acid dissolved in ethanol. After removing of the solvent, the salt is crystallized from ethyl acetate/methanol.

M.p. 187°–188° C.

The compounds of the following Examples 129 to 154 are obtained following a similar procedure, starting from the corresponding derivatives of formula I wherein Ar is as above, $R^1$ is as above but different from hydrogen, and R is hydrogen:

EXAMPLE 129:
1-(2-methylethyl)-5-methyl-3-phenyl-4,5,6,7-tetrahydro-1H-pyrazolo/4,3-c/pyridine, methanesulfonate M.p. 227°–229° C. (ethyl ether-ethanol)

EXAMPLE 130:
1-ethyl-3-(4-fluorophenyl)-5-methyl-4,5,6,7-tetrahydro-1H-pyrazolo/4,3-c/pyridine, methanesulfonate M.p. 156°–158° C. (ethanol-ethyl ether)

EXAMPLE 131:
3-(4-fluorophenyl)-5-methyl-1-phenyl-4,5,6,7-tetrahydro-1H-pyrazolo/4,3-c/pyridine, methanesulfonate M.p. 178°–179° C. (ethyl acetate-methanol)

EXAMPLE 132:
1-(4-chlorophenylmethyl)-3-(4-fluorophenyl)-5-methyl-4,5,6,7-tetrahydro-1H-pyrazolo/4,3-c/pyridine, methanesulfonate M.p. 177°–178° C. (ethanol/ethyl ether)

EXAMPLE 133:
3-(4-fluorophenyl)-1-(4-methoxyphenylmethyl)-5-methyl-4,5,6,7-tetrahydro-1H-pyrazolo/4,3-c/pyridine, hydrochloride M.p. 240°–242° C. (methanol)

EXAMPLE 134:
3-(4-fluorophenyl)-1-(4-fluorophenylmethyl)-5-methyl-4,5,6,7-tetrahydro-1H-pyrazolo/4,3-c/pyridine, hydrochloride M.p. 264°–266° C. (ethanol)

EXAMPLE 135:
3-(4-fluorophenyl)-1-(4-methylphenylmethyl)-5-methyl-4,5,6,7-tetrahydro-1H-pyrazolo/4,3-c/pyridine, methanesulfonate M.p. 202°–203° C. (ethanol-ethyl ether)

EXAMPLE 136:
1-(3,4-dichlorophenylmethyl)-3-(4-fluorophenyl)-5-methyl-4,5,6,7-tetrahydro-1H-pyrazolo/4,3-c/pyridine M.p. 135°–136° C. (ethyl acetate)

EXAMPLE 137:
1-phenylmethyl-3-(2-thienyl)-5-methyl-4,5,6,7-tetrahydro-1H-pyrazolo/4,3-c/pyridine, methanesulfonate M.p. 190°–191° C. (ethanol-ethyl ether)

EXAMPLE 138:
3-(4-fluorophenyl)-1-(2-phenylethyl)-5-methyl-4,5,6,7-tetrahydro-1H-pyrazolo/4,3-c/pyridine M.p. 113°–114° C. (ethyl acetate)

EXAMPLE 139:
3-(4-fluorophenyl)-1-(3-phenylpropyl)-5-methyl-4,5,6,7-tetrahydro-1H-pyrazolo/4,3-c/pyridine, hydrochloride M.p. 253° C. (dec.) (methanol)

EXAMPLE 140:
3-(4-fluorophenyl)-1-n.propyl-5-methyl-4,5,6,7-tetrahydro-1H-pyrazolo/4,3-c/pyridine, methanesulfonate M.p. 200°–201° C. (ethanol-ethyl acetate)

EXAMPLE 141:
3-(4-fluorophenyl)-1-n.butyl-5-methyl-4,5,6,7-tetrahydro-1H-pyrazolo/4,3-c/pyridine, methanesulfonate M.p. 186°–187° C. (ethanol)

EXAMPLE 142:
1-(2-chlorophenylmethyl)-3-(4-fluorophenyl)-5-methyl-4,5,6,7-tetrahydro-1H-pyrazolo/4,3-c/pyridine, methanesulfonate M.p. 172°–173° C. (ethanol-ethyl ether)

EXAMPLE 143:
3-(3-trifluoromethylphenyl)-4,5,6-7,-tetrahydro-1-phenylmethyl-5-methyl-1H-pyrazolo/4,3-c/pyridine, methanesulfonate M.p. 196°–197° C. (ethanol-ethyl acetate)

EXAMPLE 144:
3-(4-fluorophenyl)-4,5,6,7-tetrahydro-5-methyl-1-(1-phenylethyl)-1H-pyrazolo/4,3-c/pyridine, hydrochloride M.p. 267°–269° C. (ethanol)

EXAMPLE 145:
4,5,6,7-tetrahydro-5-methyl-3-phenyl-1-phenylmethyl-1H-pyrazolo/4,3-c/pyridine, methanesulfonate M.p. 176°–177° C. (ethanol-ethyl ether)

EXAMPLE 146:
3-(4-chlorophenyl)-4,5,6,7-tetrahydro-5-methyl-1-phenylmethyl-1H-pyrazolo/4,3-c/pyridine, methanesulfonate M.p. 228°–229° C. (ethanol-ethyl ether)

EXAMPLE 147:
4,5,6,7-tetrahydro-5-methyl-3-(4-methylphenyl)-1-phenylmethyl-1H-pyrazolo/4,3-c/pyridine, methanesulfonate M.p. 220°–221° C. (ethanol-ethyl ether)

EXAMPLE 148:
3-(4-fluorophenyl)-4,5,6,7-tetrahydro-5-methyl-1-/2-(N-methyl-2-pyrrolidinyl)ethyl/-1H-pyrazolo/4,3-c/pyridine M.p. 73°–74° C. (n-hexane)

EXAMPLE 149:
1,3-di(4-fluorophenyl)-4,5,6,7-tetrahydro-5-methyl-1H-pyrazolo/4,3-c/pyridine, methanesulfonate M.p. 226°–228° C. (ethanol)

EXAMPLE 150:
3-(4-fluorophenyl))-4,5,6,7-tetrahydro-5-methyl-1-n.pentyl-1H-pyrazolo/4,3-c/pyridine, methanesulfonate M.p. 157°–158° C. (ethanol-ethyl ether)

EXAMPLE 151:
3-(4-fluorophenyl)-4,5,6,7-tetrahydro-1-n.hexyl-5-methyl-1H-pyrazolo/4,3-c/pyridine, methanesulfonate M.p. 114°–115° C. (ethanol-ethyl ether)

EXAMPLE 152:
3-(4-ethoxyphenyl)-5-methyl-1-phenylmethyl-4,5,6,7-tetrahydro-1H-pyrazolo/4,3-c/pyridine, methanesulfonate M.p. 160°–162° C. (ethanol-ethyl ether)

EXAMPLE 153:
3-(4-fluorophenyl)-5-methyl-1-(4-nitrophenylmethyl)-4,5,6,7-tetrahydro-1H-pyrazolo/4,3-c/pyridine, methanesulfonate

EXAMPLE 154:
5-methyl-3-(4-methylthiophenyl)-1-phenylmethyl-1H-pyrazolo/4,3-c/pyridine, methanesulfonate

EXAMPLE 155:
1-(4-hydroxyphenylmethyl)-5-methyl-3-(4-fluorophenyl)-4,5,6,7-tetrahydro-1H-pyrazolo/4,3-c/pyridine, methanesulfonate

EXAMPLE 156:
1-ethyl-5-(2-methylethyl)-3-(2-thienyl)-4,5,6,7-tetrahydro-1H-pyrazolo/4,3-c/pyridine, methanesulfonate A mixture of 1-ethyl-3-(2-thienyl)-4,5,6,7-tetrahydro-1H-pyrazolo/4,3-c/pyridine (5 g; 0.0214 mole), potassium iodide (3.33 g; 0.0214 mole), potassium carbonate (11.83 g; 0.0856 mole) and 2-bromopropane (4.02 ml; 0.0428 mole) in methylethylketone (214 ml) is refluxed for 24 hours. The solvent is evaporated and the residue is taken up with water and extracted with methylene chloride. The organic phase is subsequently washed with water, dried and the solvent is evaporated under reduced pressure. The residue is purified through a short silica-gel column using a mixture of 2% methanol, in methylene chloride as the eluent.

The free base so obtained is transformed into the corresponding methanesulfonate adding an equimolecular amount of methansulfonic acid in ethanol.

M.p. 224°–225° C. (ethanol)

EXAMPLE 157:
3-(4-fluorophenyl)-5-(2-methylethyl)-1-phenyl-4,5,6,7-tetrahydro-1H-pyrazolo/4,3-c/pyridine, hydrochloride The compound is obtained essentially following the procedure of the above Example 156 starting from 3-(4-fluorophenyl)-1-phenyl-4,5,6,7-tetrahydro-1H-pyrazolo/4,3-c/pyridine.

M.p. 258°–260° C. (ethyl acetate-methanol)

EXAMPLE 158:
1-ethyl-3-(4-fluorophenyl)-5-phenylmethyl-4,5,6,7-tetrahydro-1H-pyrazolo/4,3-c/pyridine, methanesulfonate A mixture of 1-ethyl-3-(4-fluorophenyl)-4,5,6,7-tetrahydro-1H-pyrazolo/4,3-c/pyridine (55 g; 0.0204 mole), potassium iodide (0.34 g), potassium carbonate (5.63 g; 0.0408 mole), and benzylbromide (2.42 ml; 0.0204 mole) in acetone (75 ml) is refluxed for 4 hours. Following the work-up procedure of the above Example 156; the product of the title is obtained.

M.p. 206°–207° C. (ethanol)

Following a similar procedure, the compounds of Example 159 to 164 are obtained, starting from the corresponding derivatives of formula I wherein Ar is as above, $R^1$ is as above but different from hydrogen, and R is hydrogen, and using the appropriate alkylating agent.

EXAMPLE 159:
1-(2-methylethyl)-3-phenyl-5-phenylmethyl-4,5,6,7-tetrahydro-1H-pyrazolo/4,3-c/pyridine, methanesulfonate M.p. 167°–169° C. (ethanol-ethyl ether)

EXAMPLE 160:
3-(2-furanyl)-1-(2-methylethyl)-5-phenylmethyl-4,5,6,7-tetrahydro-1H-pyrazolo/4,3-c/pyridine, methanesulfonate M.p. 168°–169° C. (ethanol-ethyl ether)

EXAMPLE 161:
5-n.butyl-3-(4-fluorophenyl)-1-phenylmethyl-4,5,6,7-tetrahydro-1H-pyrazolo/4,3-c/pyridine, hydrochloride M.p. 226°–228° C. (ethanol-ethyl ether)

EXAMPLE 162:
3-(4-fluorophenyl)-5-(2-methylethyl)-1-phenylmethyl-4,5,6,7-tetrahydro-1H-pyrazolo/4,3-c/pyridine M.p. 115°–116° C. (ethyl ether)

EXAMPLE 163:
5-cyclopentyl-3-(4-fluorophenyl)-1-phenylmethyl-4,5,6,7-tetrahydro-1H-pyrazolo/4,3-c/pyridine, hydrochloride M.p. 240°–243° C. (ethanol/ethyl ether)

EXAMPLE 164:
4-/3-(4-fluorophenyl)-1-phenylmethyl-4,5,6,7-tetrahydro-1H-pyrazolo/4,3-c/pyridin-5-yl/-1-(4-fluorophenyl)-1-butanone, hydrochloride A mixture of 3-(4-fluorophenyl)-1-phenylmethyl-4,5,6,7-tetrahydro-1H-pyrazolo/4,3-c/pyridine (8 g; 0.026 mole), potassium iodide (4.32 g; 0.026 mole), potassium carbonate (10.78 g; 0.078 mole), 4-chloro-p-fluorobutyrophenone (6.79 g; 0.0338 mole) and methylethylketone (260 ml) is refluxed for 18 hours. The obtained mixture is worked-up as described in the previous Example 156. M.p. 227°–229° C. (ethanol)

Following a similar procedure the compounds of Examples 165 to 170 are obtained starting from the corresponding derivatives of formula I wherein R is an hydrogen atom:

EXAMPLE 165:
4-/3-phenyl-1-(2-methylethyl)-4,5,6,7-tetrahydro-1H-pyrazolo/4,3-c/pyridin-5-yl/-1-(4-fluorophenyl)-1-butanone, methanesulfonate M.p. 175°–177° C. (ethanol)

EXAMPLE 166:
4-/3-(4-fluorophenyl)-4,5,6,7-tetrahydro-1-phenyl-1H-pyrazolo/4,3-c/pyridin-5-yl/-1-(4-fluorophenyl)-1-butanone, methanesulfonate M.p. 223°–225° C. (ethanol-ethyl ether)

EXAMPLE 167:
4-/3-(4-fluorophenyl)-4,5,6,7-tetrahydro-1-ethyl-1H-pyrazolo/4,3-c/pyridin-5-yl/-1-(4-fluorophenyl)-1-butanone M.p. 93°–95° C. (ethyl ether)

EXAMPLE 168:
4-/3-(2-thienyl)-4,5,6,7-tetrahydro-1-ethyl-1H-pyrazolo/4,3-c/pyridin-5-yl/-1-(4-fluorophenyl)-1-butanone, methanesulfonate M.p. 143°-144° C. (ethanol-ethyl ether)

EXAMPLE 169:
4-/3-(4-fluorophenyl-1-(4-fluorophenylmethyl)-4,5,6,7-tetrahydro-1H-pyrazolo/4,3-c/pyridin-5-yl/-1-(4-fluorophenyl)-1-butanone, hydrochloride M.p. 230° C. (dec) (ethanol-ethyl ether)

EXAMPLE 170:
4-/1-phenylmethyl-3-(2-thienyl)-4,5,6,7-tetrahydro-1H-pyrazolo/4,3-c/pyridin-5-yl/-1-(4-fluorophenyl)-1-butanone, hydrochloride M.p. 248°-250° C. (ethanol-ethyl ether)

EXAMPLE 171:
4-/3-(4-fluorophenyl)-1-phenylmethyl-4,5,6,7-tetrahydro-1H-pyrazolo/4,3-c/pyridin-5-yl/-1-(4-fluorophenyl)-1-butanol, hydrochloride To a stirred solution of 4-/3-(4-fluorophenyl)-1-phenylmethyl-4,5,6,7-tetrahydro-1H-pyrazolo/4,3-c/pyridin-5-yl/-1-(4-fluorophenyl)-1-butanone hydrochloride (the compound of Example 164) (6.2 g; 13.15 mmole) in anhydrous methanol (124 ml) sodium borohydride (2 g; 52.6 mmole) is added portionwise at about 5° C., the temperature is kept at 10° C. for 1 hour. After adding ice-water (120 ml) the solvent is taken off in vacuo and the residue is extracted with ethyl acetate. The organic layer is washed with water, dried over sodium sulfate and the solvent is evaporated under reduced pressure. The residue is dissolved in methanol and treated with an equimolar amount of hydrochloric acid in methanol. M.p. 213°-214° C. (methanol-ethyl ether)

Following essentially the procedure of the above example 171 and employing the proper starting materials the following compounds of examples 172-174 were synthetized:

EXAMPLE 172:
4-/1-ethyl-3-(4-fluorophenyl)-4,5,6,7-tetrahydro-1H-pyrazolo/4,3-c/pyridin-5-yl/-1-(4-fluorophenyl)-1-butanol, hydrochloride M.p. 175°-176° C. (ethanol ethyl ether)

EXAMPLE 173:
4-/3-(4-fluorophenyl)-1-(4-fluorophenylmethyl)-4,5,6,7-tetrahydro-1H-pyrazolo/4,3-c/pyridin-5-yl/-1-(4-fluorophenyl)-1-butanol, hydrochloride M.p. 187°-188° C. (ethanol ethyl ether)

EXAMPLE 174:
4-/1-phenylmethyl-3-(2-thienyl)-4,5,6,7-tetrahydro-1H-pyrazolo/4,3-c/pyridin-5-yl/-1-(4-fluorophenyl)-1-butanol, hydrochloride M.p. 183°-184° C. (ethanol ethyl ether)

EXAMPLE 175:
1,N,N-triethyl-3-(4-fluorophenyl)-4,5,6,7-tetrahydro-1H-pyrazolo/4,3-c/pyridin-5-yl/(2-ethylamine), dihydrochloride To a stirred solution of 1-ethyl-3-(4-fluorophenyl)-4,5,6,7-tetrahydro-1H-pyrazolo/4,3-c/pyridine, methansulfonate (the compound of Example 94) (7.1 g; 29 mmole) in anhydrous dimethylformamide (71 ml) 55% sodium hydride in mineral oil (2.92 g; 60.9 mmole) is added portionwise at about 10° C., the temperature is kept at 50° C. for 30 minutes and subsequently lowered to 20° C. 2-Diethylaminoethylchloride hydrochloride (5.49 g; 31;9 mmole) is added portionwise. The temperature is kept at 60° C. for 14 hours. After adding a few drops of methanol, the solvent is taken off in vacuo and the residue is diluted with ice-water and extracted with methylene chloride. The organic layer is washed with water dried over sodium sulfate and evaporated under reduced pressure. The residue is dissolved in ethyl ether and treated with the double molar amount of hydrochloric acid in methanol.

M.p. 241°-143° C. (ethanol ethyl ether).

Essentially following the procedures of Example 1 and 19 respectively, the following compounds are prepared, starting from the proper starting materials:

EXAMPLE 176:
5-acetyl-4,5,6,7-tetrahydro-3-(4-pyridyl)-1H-pyrazolo/4,3-c/pyridine M.p. 237°-239° C. (ethyl acetate)

EXAMPLE 177:
4,5,6,7-tetrahydro-3-(4-pyridyl)-1H-pyrazolo/4,3-c/pyridine, dihydrochloride M.p. 300° C. (dec.) (ethanol-water)

We claim:
1. A pyrazolo/4,3-c/pyridine having the formula

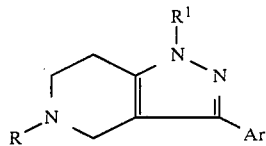

and a physiologically acceptable acid addition thereof, wherein R represents hydrogen, $(C_1-C_{10})$alkyl, $(C_3-C_7)$cycloalkyl, $(C_1-C_6)$alkanoyl, halogen$(C_1-C_6)$alkyl, $(C_1-C_4)$alkoxycarbonyl, hydroxy$(C_1-C_6)$alkyl, phenyl, phenyl substituted with from 1 to 3 substituents independently selected from chloro bromo, fluoro, cyano, nitro, hydroxy, thio, trifluoromethyl, $(C_1-C_4)$alkyl, $(C_1-C_4)$alkenyl, $(C_2-C_4)$alkynyl, $(C_3-C_7)$cycloalkyl, $(C_1-C_4)$alkoxy, $(C_1-C_2)$alkylthio, $(C_1-C_4)$alkoxycarbonyl, $(C_1-C_4)$alkylsulfinyl or a group of formula

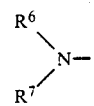

wherein $R^6$ and $R^7$ independently represent hydrogen, $(C_1-C_6)$alkyl, $(C_1-C_6)$hydroxyalkyl, $(C_1-C_4)$alkoxy, $(C_2-C_4)$alkyl, or $R^6$ and $R^7$ taken together with the adjacent nitrogen atom represent a (4-7) membered saturated heterocyclic ring which can optionally contain a further heteroatom selected from N, S, and O, and can bear a $(C_1-C_4)$alkyl group or a phenyl group optionally substituted as above, or R represents phenyl($C_1-C_6$)alkyl, substituted phenyl($C_1-C_6$)alkyl wherein the phenyl group is substituted as above, phenyl($C_1-C_6$)alkanoyl, substituted phenyl($C_1-C_6$)alkanoyl, wherein the phenyl group is substituted as above, a group of formula

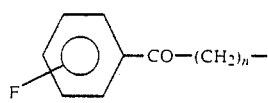

wherein n is an integer from 1 to 5 inclusive, or a group

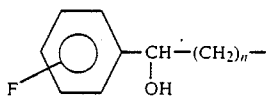

wherein n is as above; or R is a group of formula:

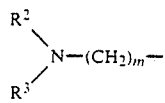

wherein m is an integer from 2 to 4 inclusive, $R^2$ and $R^3$ independently represent hydrogen, $(C_1-C_{10})$alkyl, $(C_1-C_6)$hydroxyalkyl, $(C_1-C_4)$alkoxy, $(C_2-C_4)$alkyl, or $R^2$ and $R^3$ taken together with the adjacent nitrogen atom represent a (4–7) membered saturated heterocyclic ring which can optionally contain a further heteroatom selected from N, S, and O, and can bear a $(C_1-C_4)$alkyl group or a phenyl group optionally substituted as above $R^1$ represents hydrogen, $(C_1-C_6)$alkyl, $(C_3-C_6)$cycloalkyl, phenyl, substituted phenyl wherein the phenyl ring is substituted as above, phenyl$(C_1-C_6)$alkyl, substituted phenyl$(C_1-C_6)$alkyl, wherein the phenyl group is substituted as above, or $R^1$ represents a group of formula

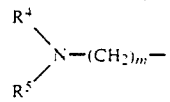

wherein m is an integer from 2 to 4 inclusive, $R^4$ and $R^5$ are as defined above for $R^2$ and $R^3$, and Ar represents a phenyl group optionally substituted as above, or Ar is a 5–6 membered heteroaromatic ring selected from the group consisting of pyrrolyl, pyridyl, 4-aminopyridyl, 4-alkylaminopyridyl, thienyl, thiazolyl, oxazolyl, pyrazolyl and furanyl, which can bear a $(C_1-_6)$alkyl or phenyl substituent.

2. A compound as in claim 1 wherein $R^1$ is hydrogen.

3. A compound as in claim 1 wherein R and $R^1$ are as above and Ar is a 4-substituted phenyl group.

4. A compound as in claim 1 in which R is hydrogen or $(C_1-C_6)$alkyl, $R^1$ is phenyl$(C_1-C_6)$alkyl wherein the phenyl group is optionally substituted as above and Ar is the 4-fluorophenyl group.

5. A CNS depressant, neuroleptic, cardiotonic, antihypertensive, analgesic or antiinflammatory composition in dosage unit form which comprises from 0.01 to 2.0 grams of a pyrazolo[4,3-c]pyridine according to claim 1 in combination with a pharmaceutically acceptable carrier.

* * * * *